(12) United States Patent
Hall et al.

(10) Patent No.: US 6,365,413 B1
(45) Date of Patent: Apr. 2, 2002

(54) THIN FILM THERMAL OXIDATIVE OIL DEPOSIT TESTING DEVICE AND METHOD

(75) Inventors: Richard H. Hall; David A. Dalman; Theodore W. Selby; Jennifer J. Richardson, all of Midland, MI (US)

(73) Assignee: Savant, Inc., Midland, MI (US)

( * ) Notice: Subject to any disclaimer, the term of this patent is extended or adjusted under 35 U.S.C. 154(b) by 0 days.

(21) Appl. No.: 09/258,114

(22) Filed: Feb. 25, 1999

Related U.S. Application Data

(60) Provisional application No. 60/076,295, filed on Feb. 27, 1998.

(51) Int. Cl.$^7$ .......................... G01N 33/30; G01N 33/26
(52) U.S. Cl. .................... 436/60; 73/53.05; 73/53.06; 73/53.07; 73/61.62; 203/31; 203/38; 203/89; 159/12; 159/13.3; 422/53; 422/68.1; 422/80; 436/6
(58) Field of Search .................. 436/6, 60; 422/53, 422/68.1, 80; 73/53.05, 53.07, 61.62, 865.5; 203/31, 38, 89; 159/12–13.3

(56) References Cited

U.S. PATENT DOCUMENTS

| | | | |
|---|---|---|---|
| 1,925,559 A | * | 9/1933 | Hickman |
| 1,932,405 A | * | 10/1933 | Harris |
| 1,942,858 A | * | 1/1934 | Hickman |
| 2,126,467 A | * | 8/1938 | Hickman et al. |
| 2,221,691 A | * | 11/1940 | Hickman |
| 2,363,247 A | * | 11/1944 | Holder |
| 2,370,462 A | * | 2/1945 | Hecker |
| 2,530,376 A | * | 11/1950 | Castle et al. |
| 2,732,285 A | | 1/1956 | Lynch et al. ................. 436/60 |
| 3,031,401 A | * | 4/1962 | Thayer |
| 3,044,860 A | | 7/1962 | Verley ........................ 436/60 |
| 3,615,288 A | * | 10/1971 | Sweeney et al. |
| 3,705,014 A | * | 12/1972 | Townsley |
| 4,032,462 A | | 6/1977 | Hotten et al. ............... 252/49.7 |
| 4,745,070 A | | 5/1988 | Korcek et al. ................ 436/60 |
| 5,287,731 A | | 2/1994 | Florkowski et al. ..... 723/53.05 |
| 5,401,661 A | | 3/1995 | Florkowski et al. ........... 436/6 |

FOREIGN PATENT DOCUMENTS

JP 58-162865 * 9/1983

OTHER PUBLICATIONS

Federal Test Methods No. 791B Method 5003.1, 1969.*

(List continued on next page.)

*Primary Examiner*—Arlen Soderquist
(74) *Attorney, Agent, or Firm*—Christopher John Rudy

(57) ABSTRACT

Thin film thermal oxidative engine oil or other oleaginous liquid deposit device has an oleaginous test liquid placement volume; a heatable depositor surface in liquid communication with the volume; a supply for at least one of an oxidant and another substance which can adversely affect the test liquid; and a relatively thin film forming unit which delivers the test liquid to the depositor surface in a relatively thin film. Thin film thermal oxidative engine oil or other oleaginous fluid deposit method is also provided, which includes providing an oleaginous test liquid in an oleaginous test liquid placement volume; providing a depositor surface and heating said surface; delivering the test liquid as a relatively thin film to the heated depositor surface; providing to the test liquid an oxidizing and/or other substance which can adversely affect the test liquid; and observing any deposits or other activity thereabout. The invention is useful in oil testing.

30 Claims, 6 Drawing Sheets

OTHER PUBLICATIONS

S. A. McKee et al, Anal. Chem. 1949, 21, 568–572.*
D. J. W. Kreulen J. Inst. Petrol. 1951, 37, 316–323.*
H. Mourski NAFTA 1952, 8, 186–188.*
H. L. Hepplewhite et al, Proc. USAF Aerospace Fluids lubricancts Conf., San Antonio 1963, 62–69.*
K. K. Papok et al, Khim. Teckhnol. Topl. Masel 1971, 16, 51–54.*
I. M. Pievskii et al, Teplomassoperenos Odno–Dvukhfaznykh Sredakh 1983, 92–98.*
Idemitsu Kosan Co., Ltd. Chem. Abstr. 1984, 100, abstract 106368z, Apr. 1984.*
Tannas Co., Catalog, May 1994, pp. 4–5.*
M. Valtierra et al, NBS Spec. Publ. 1980, 584, 205–219, Nov. 1980.*
D. W. Florkowski et al, Soc. Automot. Eng. 1993, SP–996, 271–288.*
J, Xie et al, Shiyou Xuebao, Shiyou Jiagong Mar. 1995, 11, 98–103.*
H. Moritani et al, Soc. Automot. Eng. 1995, SP–1116, 153–159.*
A. U. C. Maduako et al, Tribol. Int. 1996, 29, 153–160, May 1994.*
C.–S. Ku et al., *Lubr. Eng.,* 1984, 40, 75–83.
J. Xie et al., *Chem. Abs.,* 1995, 123, 60878k, 60879m.
H. Moritani et al., *Chem. Abs.,* 1996, 124, 92131y.
A.U.C. Maduako et al., *Chem. Abs..,* 1996, 124, 293799w.
H. Moritani, *Chem. Abs.,* 1997, 126, 20674w.
Z. He et al., *Chem. Abs.,* 1997, 127, 68208v.
Z. He et al., *Chem. Abs.,* 1997, 127, 68211r.
Selby, T., Florkowski, D., "The Development of the TEOST Protocol MHT Bench Test of Engine Oil Piston Deposit Tendency," Paper Presented at the 12th Esslingen Colloquim, Esslingen, Germany, 3pp., Jan. 11–13, 2000 A.D.

* cited by examiner

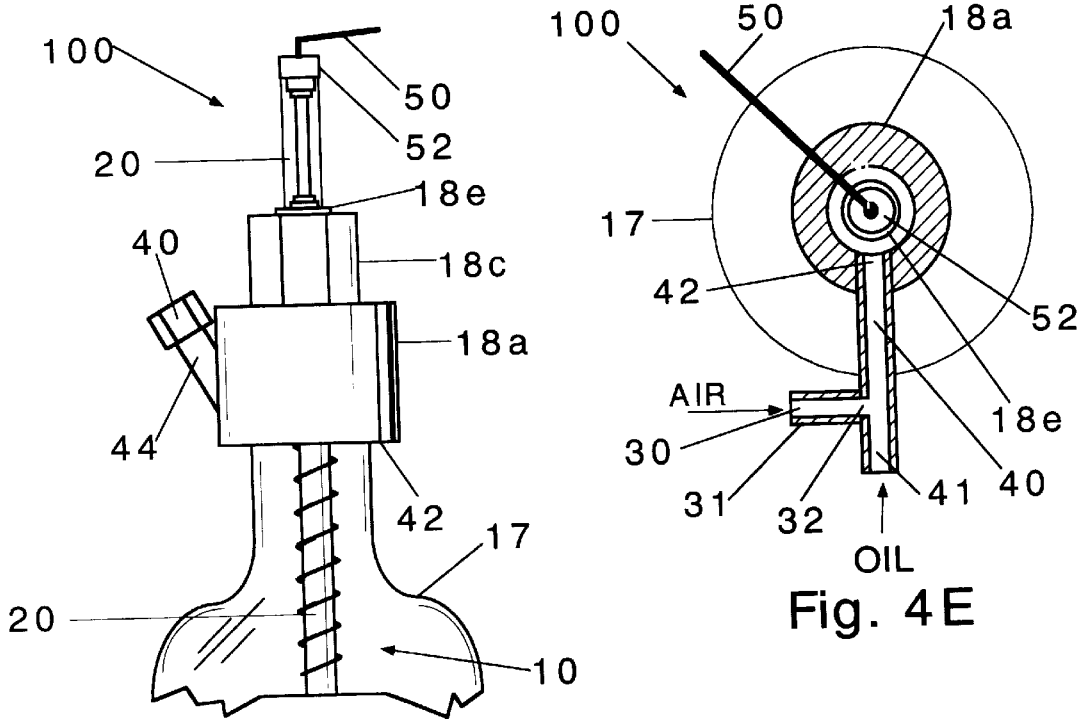
Fig. 4C
Fig. 4E
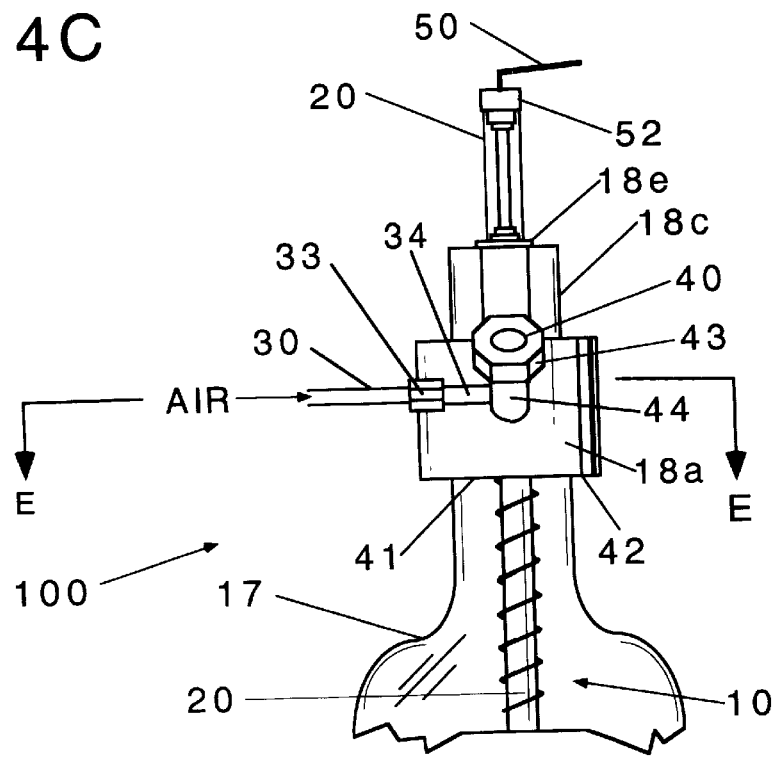
Fig. 4D

THIN FILM THERMAL OXIDATIVE OIL DEPOSIT TESTING DEVICE AND METHOD

PRIORITY

The benefit under 35 USC 119(e) is claimed of Hall et al., U.S. provisional patent application No. 60/076,295 filed Feb. 27, 1998 A.D. Its specification is incorporated herein by reference.

FIELD

Of concern is an apparatus and method useful in employment in testing engine oils and other oleaginous liquids, by use of heat and oxidation and/or other adverse effect to form deposits. The sample oil or other oleaginous fluid is passed in a relatively thin film over a heated surface and from it, deposits are formed on the heated surface.

BACKGROUND

Florkowski et al., U.S. Pat. No. 5,287,731 (Feb. 22, 1994) & U.S. Pat. No. 5,401,661 (Mar. 28, 1995), disclose thermo-oxidation engine oil simulation testing. Such testing mimics turbocharger conditions.

Selby et al., U.S. patent application Ser. No. 08/995,720 filed on Dec. 22, 1997, discloses a thermo-oxidation engine oil simulation test apparatus and method. Such apparatus and method addresses laboratory simulation of internal combustion engine conditions, and a fluid which can have an adverse effect on the oil, for an example, nitric oxide, is added therewith.

That art employs bulk flow generation of deposits. Typically employed in such testing is about twenty hours or more per run.

It would be desirable to improve over such useful art.

SUMMARY

The present invention provides, in one aspect, a thin film thermal oxidative engine oil or other oleaginous liquid deposit device (apparatus) comprising an oleaginous test liquid placement volume; a heatable depositor surface in liquid communication with said volume; a supply for at least one of an oxidant and another substance which can adversely affect said liquid; and a relatively thin film forming unit which delivers said liquid to said surface in a relatively thin film. In another aspect, a thin film thermal oxidative engine oil or other oleaginous fluid deposit method is provided, which comprises providing an oleaginous test liquid in an oleaginous test liquid placement volume; providing a depositor surface and heating said surface; delivering said liquid as a relatively thin film to the heated depositor surface; providing to said liquid an oxidizing and/or other substance which can adversely affect said liquid; and observing any deposits or other activity thereabout.

The invention is useful in oil testing.

By the invention, testing of engine oils and other oleaginous liquids in vastly improved. The amount of tent liquid required can be greatly reduced.

Numerous further advantages attend the invention.

DRAWINGS

The drawings form part of the specification hereof. With respect to the drawings, the following is briefly noted:

FIGS. 3A, 3B, 3C, 3D, 3E, 3F & 3G are side views of depositor surfaces in forms of a generally smooth rod (FIG. 3A), a knurled rod (FIG. 3B), a threaded rod (FIG. 3C), a threaded rod adjacent a tube wall (FIG. 3D), a spring wound about a smooth rod cylinder (FIG. 3E-i) with a view of the spring itself (FIG. 3E-ii), say, of annealed steel and flat, half-rounded or rounded, a flat plate (FIG. 3F), and a helically troughed rod (FIG. 3G) through which, for example, a low viscosity oil winds down in a thin film, for employment in the practice of the invention.

Figure 4A:
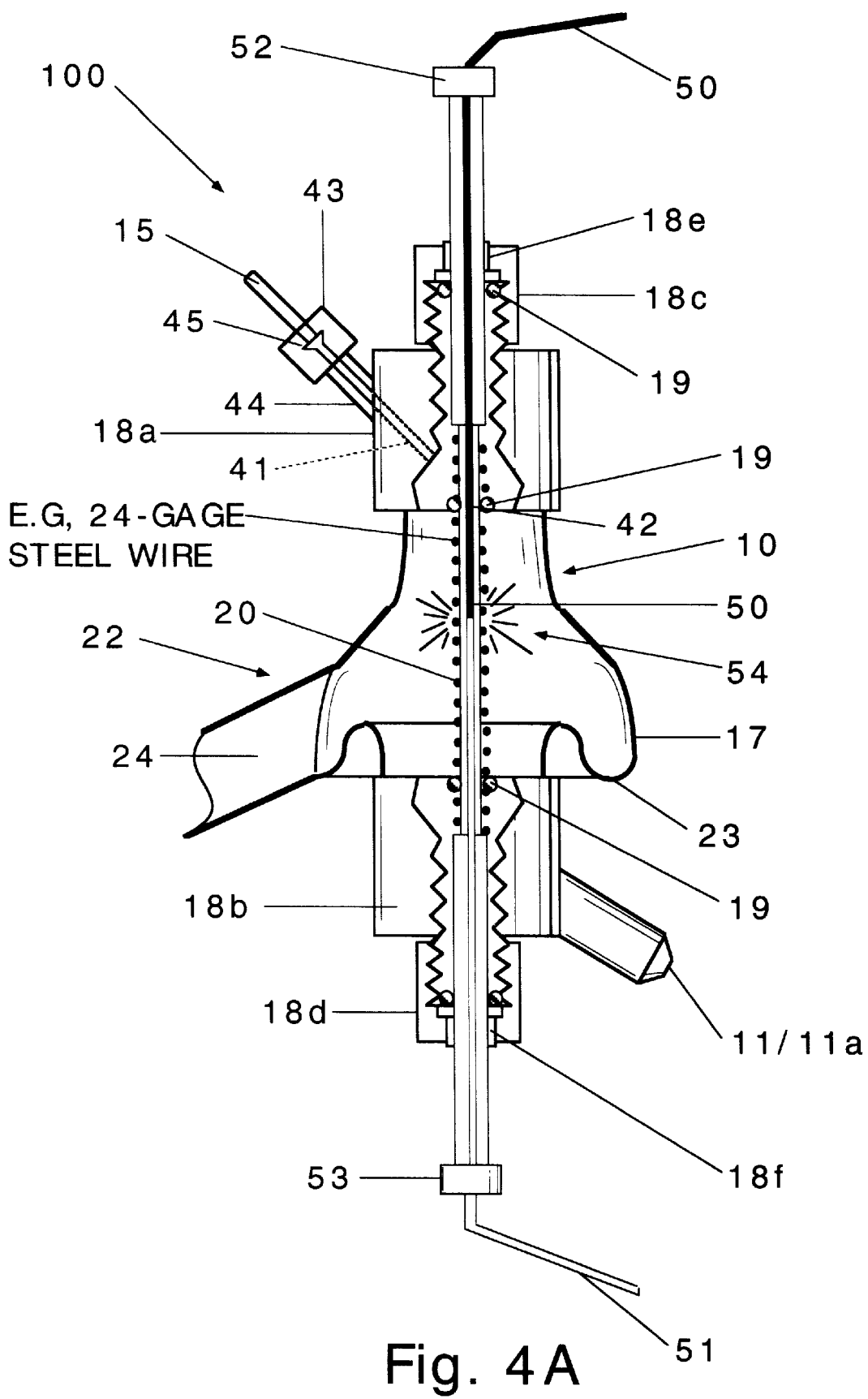
Figure 4B:
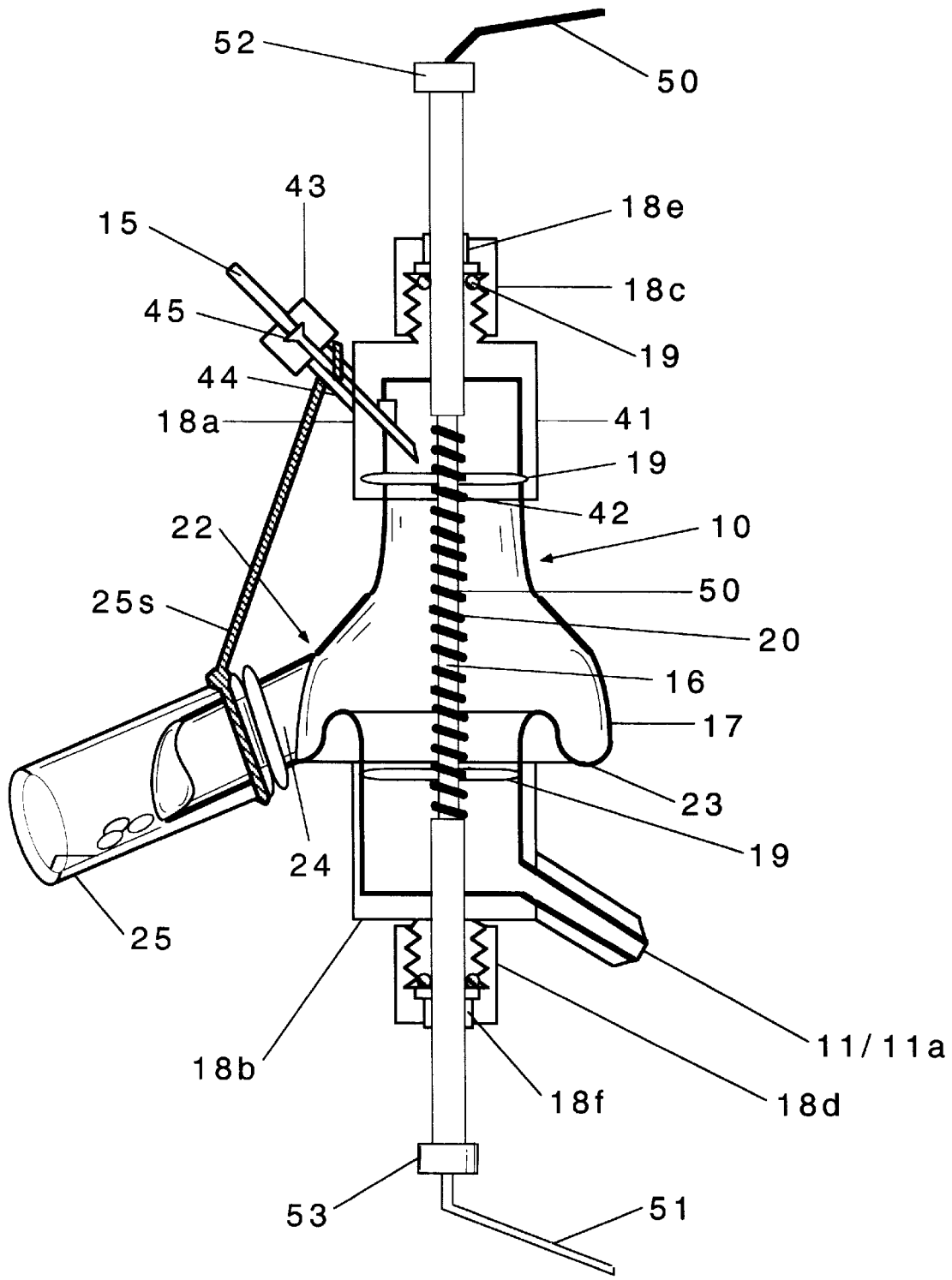
Figure 4F:
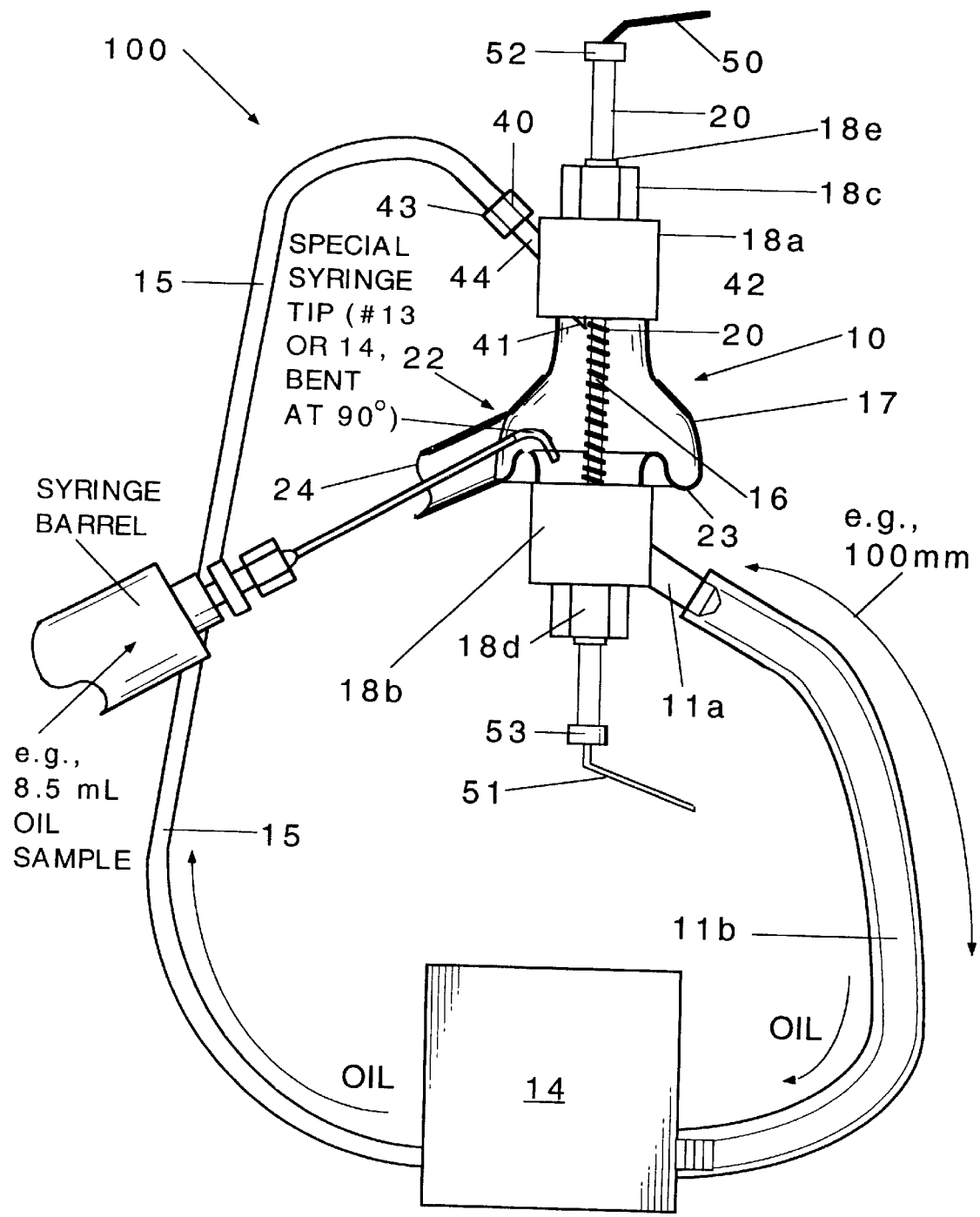

FIGS. 4A, 4B, 4C, 4D, 4E, & 4F are plan views (A, B, C, D & F) and a top schematic view (E), with the same in at least part cross section, of another embodiment of an apparatus of the invention. More particularly, FIG. 4A shows a depositor assembly in a cut-away, side view; FIG. 4B shows, among other things, insertion of an oil inlet tube in a cut-away, side view of the assembly; FIG. 4C shows detail of an upper mantle end cap, in a front view of part of the assembly; FIG. 4D shows detail of the upper mantle end cap, in a side view of part of the assembly; FIG. 4E shows the top, in a schematic, cut-away view of part of the assembly, taken along E—E in FIG. 4D; and FIG. 4F, among other things, shows injection technique with the assembly, in a cut-away, side view.

ILLUSTRATIVE DETAIL

The invention can be further understood by the present detail which may be read in view of the drawings. The same is to be understood in an illustrative and not necessarily limiting sense.

With reference to the drawings, in general, thin film thermal oxidative engine oil or other oleaginous liquid deposit apparatus 100 has oleaginous test liquid placement volume 10; heatable depositor surface 20 in liquid communication with the volume 10;

supply 30 for at least one of an oxidant and another substance which can adversely affect said liquid; and relatively thin film forming unit 40 which delivers said liquid to the surface 20 in a relatively thin film. Examples of oleaginous liquids other than engine oil which may be employed in the invention include automatic transmission fluid, sewing machine oil, engine oil base stock, manual transmission oil, and so on. The apparatus of this invention may be practiced with a device modified from that disclosed by the patents to Florkowski et al., or by the utility patent application of Selby et al., the specifications of these patents and that utility patent application being incorporated herein by reference, which are devices commercially available as the TROST (Reg. U.S. Pat. & Tm. Off.) apparatus from Tannas Co., Midland, Mich., U.S.A. Alternatively, the apparatus may be constructed from the ground up so as to more adaptively embody certain advantageous features hereof.

Figure 1:
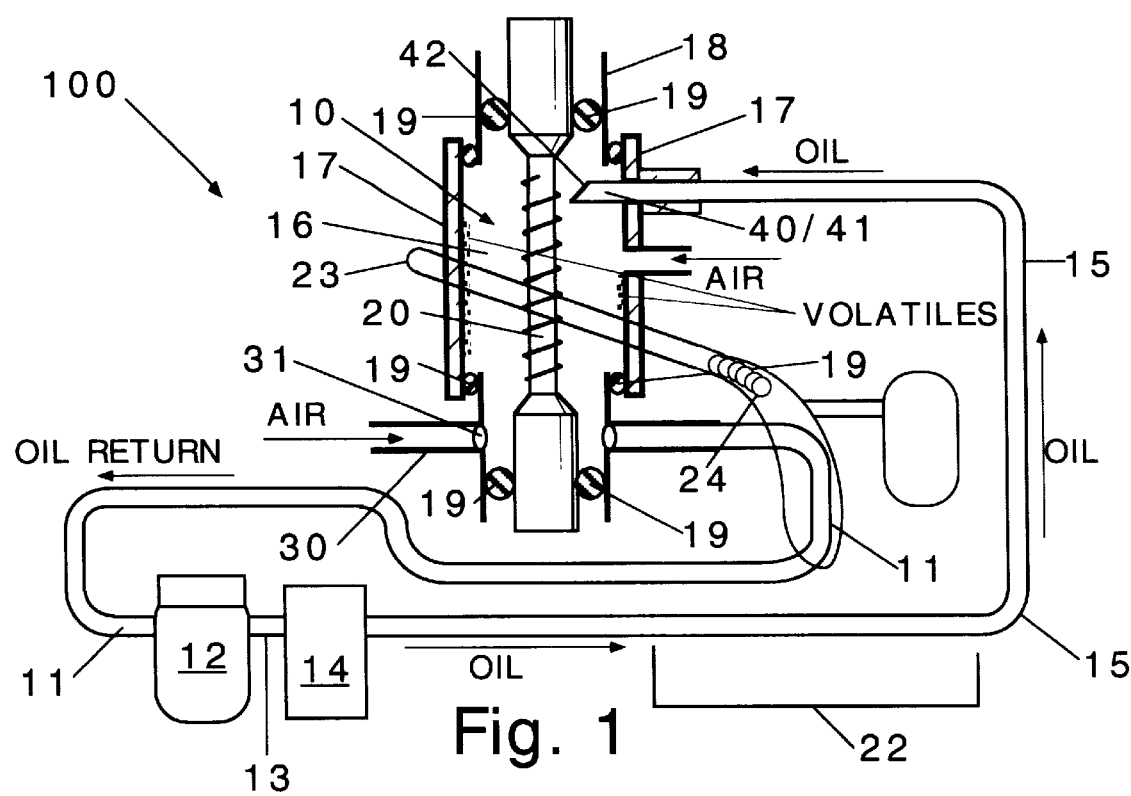
FIG. 1 is a side plan view of an apparatus of the invention.
Figure 2:
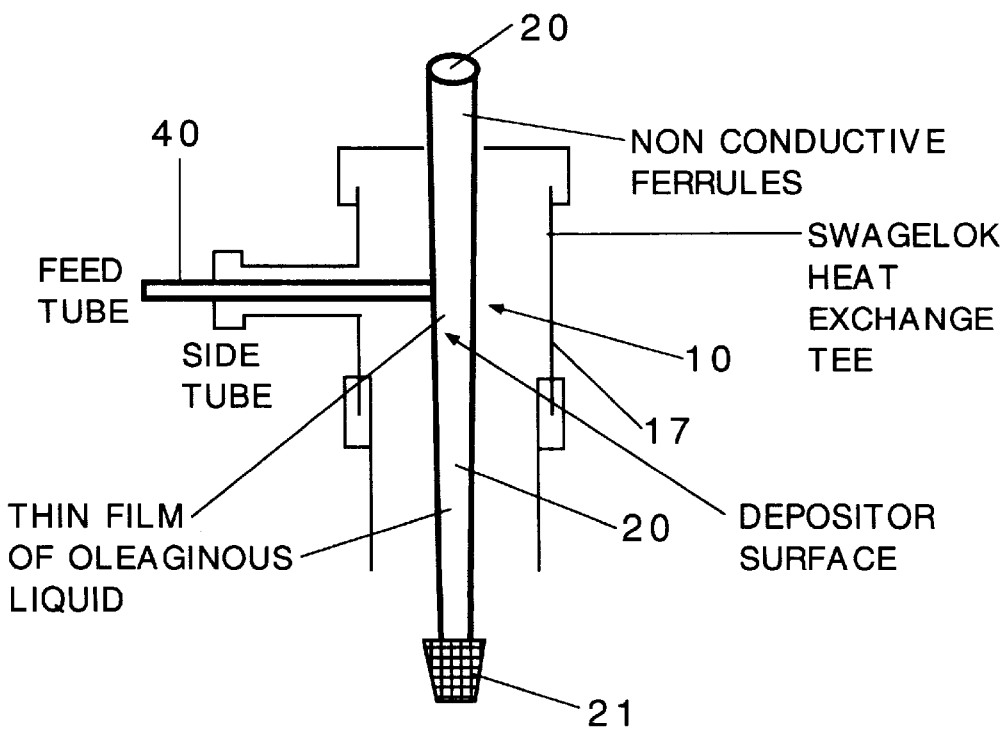
FIG. 2 is a side plan view of another embodiment of an apparatus of the invention.

As shown in FIG. 1, the volume 10 may include return line 11; reservoir 12, which may be substantially small or even be simply part of the liquid communication lines of the device; first supply line 13; pump 14; second supply line 15; and depositor surface area 16. These may be made of any suitable material, for example, stainless steel and/or glass. As shown in FIGS. 1 & 2, the depositor surface area 16 includes see-through wall 17, for example, of a high-temperature glass such as VYCOR or PYREX. The wall 17 may be in the form of a tube which envelopes stainless steel tube 18 and is sealed therewith by O-rings 19, for example, of VITON high-temperature elastomer material. The volume 10 can be about that of the testing devices of Florkowski et al., or of Selby et al., or be such that as little as fifty, twenty, ten, or five grams of liquid sample are employed. In FIG. 4 (A, B & F) is seen the volume 10 about the heatable surface depositor rod 20 with wound wire; return line 11, which can be of a glass outlet orifice or bottom end cap 11a that enters into a transparent flexible bottom end cap drain tube 11b, for example, with about a 100-mm or slightly more length and 9.5-mm inner diameter, which can serve as a small pump supply line and reservoir to hold at least a part of an oil sample, e.g., 8.5 mL, employed, which eliminates the pot reservoir of the TEOST (Reg. U.S. Pat. & Tm. Off.) unit disclosed by the patents to Florkowski et al., and permits smaller sample size employment; thin-film-forming unit oleaginous liquid supply line or oil feed tube 15, for example, a 3.2-mm rigid fluorinated polyethylene tube piece connected to a 3.2-m oil outlet orifice of the pump 14 and extending a 254-mm length from the pump 14; the depositor surface area 16 which includes hollow, generally pear-shaped glass mantle 17, the ends of which are generally closed by upper or top end cap 18a and lower or bottom end cap 18b that can include threads for threading engagement with top and bottom end cap nuts 18c & 18d, respectively. Isolators 18e, 18f such as of ceramic, may be employed to keep a depositor rod 20 in place and insulate its heat from the end cap nuts 18c, 18d. O-rings 19 seal the assembly. The O-rings 19 are suitably sized, and can be employed in sets; for example, O-rings for the end caps 18a, 18b are generally larger than the O-rings for the end cap nuts 18c, 18d, e.g., 19-mm outer diameter by 0.17-mm torus cross-section versus 8-mm outer diameter by 0.17-mm torus cross section, and the O-rings for the two end caps can be employed singly with the O-rings for the two end cap nuts employed in pairs.

The heatable depositor surface 20 may be in the form of a rod (FIGS. 2 & 3A); a Knurled rod (FIG. 3B); a standard SAE-threaded rod (FIG. 3C); a modified-ACME threaded rod (FIG. 3D); a spring wound about a smooth rod (FIGS. 1 & 3E); or even a flat plate (FIG. 3F) or a helically-oriented trough about a rod (FIG. 3O) through which an oleaginous liquid, especially a low viscosity liquid, is channeled and is carried. Preferably, the depositor surface 20 comprises a steel tube or hollow rod which has a steel wire wound about it (FIGS. 4A–F). Other alternatives (not illustrated) may include a sand-blasted rod, a vertically grooved rod, and a standard ACME-threaded rod. The depositor surface 20 is made of any suitable material, preferably, metal, for example, stainless steel. Heating may be provided by electrical resistance of the depositor surface 20 with electric current running therethrough, for example, with the rod-shaped embodiments, and/or by electric resistance heating in block 21 adjacent the surface 20, for example, as with the flat plate embodiment. One example of the depositor surface 20 is a generally cylindrical steel rod, about six and three eighths of an inch in length with end diameters of about 0.186 inches; a centrally positioned cylindrical section about two and five sixteenths or an inch in length with a diameter of about 0.127 inches; having a steel wire spring encircling the central section, which spring is about one to one and one-half inches in length, say, as may be provided by a one-inch helical music wire spring: 0.180 inches in outside diameter, 0.026 inches in wire diameter, and about ten to twenty or so coils to the inch, about an inch in length before installation onto the rod. Preferably, that rod is helically wound about its central portion with a therefore steel wire which has a wound helix axial length of two inches and has thirteen turns of the wire in that two-inch length. Auxiliary deposit collecting basket 21 (FIG. 2) may be employed. As a further option, volatiles collection system 22 can include the following (FIG. 1): depositor surface area groove 23, which may be be concave or convex as taken from the internal point of view; volatiles collection shunt 24 leading to volatiles collection trap 25; and/or oxygen uptake monitor 26. Preferably, the volatiles collection system 22 includes the following (FIGS. 4A, 4B, 4F): glass mantle lower end collection trough 23 leading to volatiles delivery tube 24: condensed volatiles collection vial or bottle 25, for example, of a 16-mL size and of glass, which can be placed over the volatiles delivery tube 24 and secured in place by volatiles collection bottle securing strap or vial clip 25s, which can be under tension and hold the vial 25 in place, say, by connecting it by setting the clip 25s over part of the top end cap 18a. In general, the oleaginous liquid, for example, oil component, which volatilizes from the heated rod 20 gathers on the inner wall of the mantle 17, drains to the trough 23 and from thence flows to the delivery tube 24 and into the vial 25. Generally, thus, condensed liquid volatiles are collected.

The supply 30 for at least one of an oxidant and another substance which can adversely affect said liquid may include unit 31 in the form of a tube through which air, oxygen-enriched air, pure oxygen, ozone, and so forth is delivered to the test sample in the apparatus. Optionally, the other substance which can adversely affect the test sample liquid may be provided through the same tube-like unit 31 or another similar separate unit (FIG. 1), which can deliver a suitable gas or liquid, for example, air, say, in an upper inlet 31, or an oxide of nitrogen, to include nitric oxide and/or nitrous oxide, for an example, the nitric oxide, or sulfur trioxide. The upper unit 31 alternatively delivering air rather than delivery from a lower unit 31 (FIG. 1) of the system can push oil to the bottom of the apparatus with no bubbling of oil up into the volatiles collection shunt 24. Provision may be through orifice 32, and the tube may be secured by air inlet nut 33 which tightens over air inlet stem 34 (FIG. 4E). As an alternative, the same may be provided by incorporating a chemical oxidant, oxygen-releasing substance, or other material which can release the other substance which can adversely affect the test sample liquid, to include hydrogen peroxide, benzoyl peroxide, di-tert-butylperoxide, di-cumylperoxide, cumene hydroperoxide, tert-butylperoctoate, 2-ethylhexylnitrate, and so forth. Combinations thereof may be employed. For example, di-tert-butylperoxide can be employed in the test liquid, with air and nitric oxide being supplied separately around the depositor rod surface 20. Preferably, air is delivered, for example, at an about 2-mL per minute flow rate to the upper portion of the glass mantle 17 without causing the entering air to bubble through the oil supply tube 41 but rather causing it to enter alongside the tube 41 and into the interior of the mantle 17 (FIG. 4E).

Figure 3A:
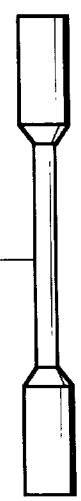
Figure 3B:
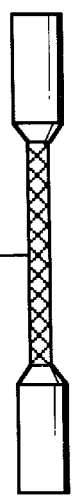
Figure 3C:
Figure 3D:
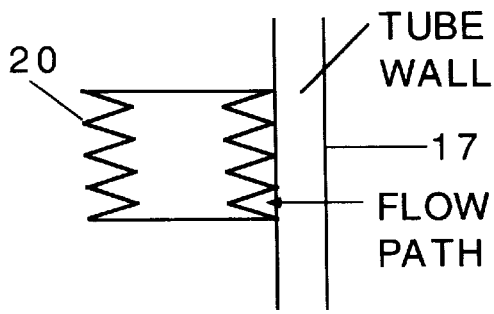
Figure 3F:
Figure 3F:
Figure 3F:
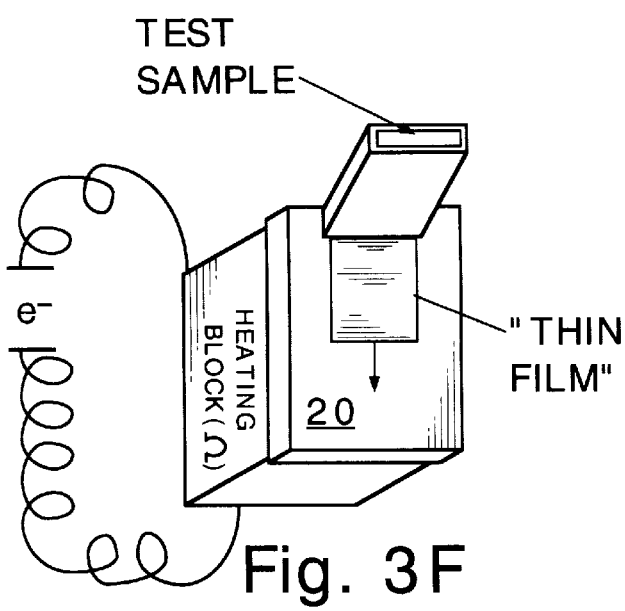
Figure 3G:
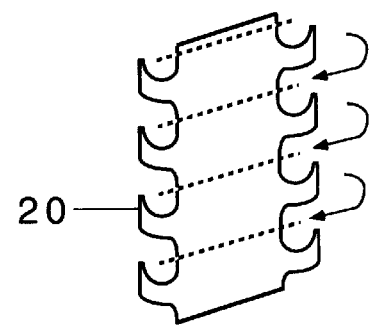

The relatively thin film forming unit 40 delivers the test liquid to the depositor surface 20 at a rate to form a relatively thin film flowing down the surface 20, for example, with the depositor the heated, wire-wound rod (FIGS. 4A–F) rod-heated oil flows down the rod 20 generally following the wire windings. The unit 40 can be of any suitable form, for example, in form of i delivery tube 41 with beveled exit orifice 42 close to the surface 20, say, about a millimeter or less away (FIGS. 1, 2 & 4A–F). As an alternative, an extended linear orifice adjacent or close to a flat depositor surface may be employed (FIG. 3F). The relatively thin film may be provided by running the test liquid down a side of the depositor surface 20 (FIGS. 1 & 3) or by mechanical constraint such as by having the depositor surface 20 reside adjacent or close to the depositor surface area wall 17 (FIG. 3D). In general, bulk flow and its inherent difficulties in effective diffusion of the oxidizing or other substance into the body of the oleaginous test liquid are avoided, and diffusion is ameliorated or eliminated as a substantially limiting factor. For example, the relatively thin film can be in about the one thousandths of an inch thick range, depending upon the supply rate, depositor surface temperature, and viscosity of the sample, e.g., with engine oil pumped over a 285-degree C., wire-wound rod 20 from the beveled delivery tube 41, 42 (FIGS. 4A–F) at a low rate of flow such au about 0.25 grams per minute. The tube 41 may be secured with feed tube nut 43 which tightens over feed inlet stem 44. A ferrule 45, which may be of two pieces, may be employed to assist in securing and sealing the system.

Thermocouple(s) may be present. Temperature control thermocouple 50 and over temperature thermocouple 51 can be inserted into the hollow depositor rod 20 (FIGS. 4A–F). The thermocouple 50 may be employed to determine a hot spot 54 for testing. The thermocouples 50, 51 are typically secured at the ends of the rod 20 by upper and lower locking collars 52 & 53 (FIGS. 4A–F).

In the practice of the invention methodology, in general, the oleaginous test liquid is provided in an oleaginous test liquid placement volume; the depositor surface is provided and heated; the test liquid is provided as a relatively thin film to the heated depositor surface; the oxidizing and/or other substance which can adversely affect the test liquid is (are) provided; and any deposits and/or other activity, particularly about the depositor surface 20, the depositor surface area 16, and so forth, are observed. Weighing of the deposits, volatiles and/or remaining test liquid may be carried out. As well, instrumental analyses of the deposits, volatiles and/or remaining test liquid may be carried out. The method of the Invention in some basic features can be conducted analogously to that or the patents to Florkowski et al. and the patent application of Selby et al.

Be that as it may, the heating may be generally less than the methods formerly employed with the device of Florkowski et al., which could include cycling of temperatures from 400–200 degrees C. Heating herein typically includes temperatures about from two hundred to three hundred degrees C., for example, heating of the depositor rod 20 to about two hundred sixty degrees C. Preferably, however, the wire-wound rod (FIGS. 4A–F) is heated to about two hundred eighty-five degrees C., and is kept at a steady temperature, say that 285-degree C. temperature, for the duration of the test.

Times required to obtain meaningful test results may vary. Test times of about from a half hour to a hundred hours, say, about from twenty to thirty or forty hours, for example, a test time of twenty-four hours at the 285-degree C. depositor rod temperature, can be employed.

Flow rates can be reduced from those employed in the Florkowski et al., and Selby at al., methods as well. These include about from seventy-five to twenty-five percent, for instance, about five-eighths or approximately a half of those employed in the other methods. Thus, an about 0.25-g/minute flow rate can be employed (versus a 0.40-g/minute flow rate previously employed in another method employing the device disclosed by the Florkowski et al. patent).

In some embodiments hereof, liquid flow may be reversed. In particular, this may be carried out in a system in which a wall 17 and depositor 20 constrain the test liquid (e.g., FIG. 3D).

Generally, other substances may be added as well. For example, reaction aids and/or catalysts such as including ferric naphthanate with reduced levels or lead and tin from those found in the other methods may be employed. Other species which may find use herein include metals such as zinc, copper, manganese, cobalt, vanadium, and so forth.

The test sample may be employed "as is" or, as an option, be distilled so as to attempt to free a sample such as engine oil from additives to see if the more basic oil behaves differently than the oil with additives. The oils could then be reversed, i.e., added back to the other residual to compare package effect.

Operation of the system can be non-adibatic. For example, heat is provided on the depositor rod surface, not on the walls (FIG. 1).

CONCLUSION

The present invention is thus provided. Various features, subcombinations and combinations may be practiced with or without reference to other features, subcombinations or combinations of the invention, and numerous adaptations and modifications can be effected within its spirit, the literal claim scope of which is particularly pointed out as follows:

We claim:

1. A thin film thermal oxidative engine oil or other oleaginous liquid deposit device comprising an oleaginous test liquid placement volume; a heatable deposit surface in the form of a rod having a generally helical guide or channel for the test liquid such that a thin film can be formed on said surface, in which bulk flow and its inherent difficulties in effective diffusion of the oxidant of other substance into the body of the oleaginous test liquid can be avoided, and diffusion can be ameliorated or eliminated as a substantially limiting factor when said liquid is delivered to said surface by a thin film forming unit, with said surface in liquid communication with said volume; a supply for at least one of an oxidant and another substance which can adversely affect said liquid; and the thin film forming unit which delivers said liquid to said surface in said thin film.

2. The device of claim 1, wherein said rod is made of metal.

3. The device of claim 2, wherein said rod is hollow and has a wire or spring wound about it.

4. The device of claim 3, wherein the hollow of said rod is penetrated by at least one thermocouple.

5. The device of claim 4, wherein said placement volume is generally in the form of a hollow pear-shaped vessel with a top and a bottom, and having a generally annular volatiles collection trough at the bottom into which condensed volatiles can be collected during operation of the device, and a volatiles delivery tube in communication with said trough through which volatiles can be removed from said trough.

6. A method for analysis of an oleaginous fluid through employment of thin film thermal oxidative oleaginous fluid deposit, which method comprises providing an oleaginous test liquid in an oleaginous test liquid placement volume; providing a depositor surface in the form of a rod having a generally helical guide or channel for the test liquid such that a thin film can be formed on said surface, in which bulk flow and its inherent difficulties in effective diffusion of the oxidant of other substance into the body of the oleaginous test liquid can be avoided, and diffusion can be ameliorated or eliminated as a substantially limiting factor when the test liquid is delivered to said surface by a thin film forming unit, with said surface in liquid communication with said volume; heating said surface; delivering said liquid as said film to the heated depositor surface; providing to said liquid the oxidizing and/or other substance which can adversely affect said liquid; and observing any deposits or other activity thereabout, weighing the deposits.

7. The method of claim 6, wherein the oleaginous test liquid is an engine oil: the oxidizing and/or other substance which can adversely affect said liquid includes oxygen; and weighing is employed.

8. The method of claim 7, wherein said surface is in the form of a rod having a wire encircling a centrally positioned central section between the ends of the rod, and the rod is heated to about from two hundred to three hundred degrees C.

9. The method of claim 8, wherein the heating of said surface is kept constant.

10. The method of claim 9, wherein condensed volatile components are collected during testing.

11. The method of claim 6, wherein a pot reservoir is not employed.

12. The method of claim 6, wherein the thin film is about one thousandths of an inch.

13. The method of claim 12, wherein the oleaginous fluid is an engine oil, and the oxidizing and/or other substance which can adversely affect said liquid includes oxygen.

14. The method of claim 13, wherein said surface is heated to about from two hundred to three hundred degrees C.

15. The method of claim 14, wherein the heating of said surface is kept constant; a flow rate of about 0.25 g per minute of the engine oil is employed; condensed volatile components are collected during testing.

16. A thin film thermal oxidative engine oil or other oleaginous liquid deposit device comprising an oleaginous test liquid placement volume; a heatable depositor surface in liquid communication with said volume, the heatable depositor surface having a configuration to guide or channel said liquid so that said liquid has a thickness of about one thousandths of an inch when on said surface; a supply for at least one of an oxidant and another substance which can adversely affect said liquid; and a thin film forming unit which can deliver said liquid to said surface in said film.

17. The device of claim 16, wherein said depositor surface is in the form of a rod.

18. The device of claim 17, wherein said rod is hollow and has a wire or spring wound about it.

19. The device of claim 18, wherein the hollow of said rod is penetrated by at least one thermocouple, and the rod is made of metal.

20. The device of claim 19, wherein said placement volume is generally in the form of a hollow pear-shaped vessel with a top and a bottom, and having a generally annular volatiles collection trough at the bottom into which condensed volatiles, can be collected during operation of the device, and a volatiles delivery tube in communication with said trough through which volatiles can be removed from said trough.

21. A depositor surface useful for a thin film thermal oxidative engine oil or other oleaginous liquid deposit device comprising a generally cylindrical rod having opposing ends and a centrally positioned cylindrical section between the ends, and a wire encircling said centrally positioned section, said depositor surface capable of being heated.

22. The depositor surface of claim 21, wherein the rod is hollow, and the opposing ends have diameters larger than the diameter of said centrally positioned section.

23. The depositor surface of claim 22, wherein at least one thermocouple is positioned inside the rod.

24. The depositor surface of claim 23, wherein heating can be provided by electrical resistance with electric current running through the rod.

25. The depositor surface of claim 24, wherein the rod is made of metal.

26. The depositor surface of claim 25, wherein the rod is made of of steel, and the wire is a steel spring.

27. The depositor surface of claim 26, wherein the rod is about 6⅜ inches in length, with end diameters of about 0.186 of an inch; said centrally positioned section is about 2 5/16 inches in length, with a diameter of about 0.127 of an inch; and the wire is helically arranged and a helical length about from 1 inch to 2 inches in length with about 10 to 20 coils to the inch.

28. The depositor surface of claim 22, wherein the rod is about 6⅜ inches in length, with end diameters of about 0.186 of an inch; said centrally positioned section is about 2 5/16 inches in length, with a diameter of about 0.127 of an inch; and the wire is helically arranged and a helical length about from 1 inch to 2 inches in length with about 10 to 20 coils to the inch.

29. A mantle useful for a thin film thermal oxidative engine oil or other oleaginous liquid deposit device comprising a hollow body having top and bottom portions thereto, said body with openings at the top and bottom so that a depositor rod can be inserted therethrough, and said body generally in the shape of a pear; a thin film forming unit for introduction of a test liquid to the depositor rod; inside the body near the bottom and connected thereto, a lower end, upwardly facing volatiles collection trough having sides and a bottom, which trough leads to a volatiles delivery opening; and a test liquid exit orifice.

30. The mantle of claim 29, wherein said body is of glass; and top and bottom end caps and isolators are present for closing the top and bottom openings and keep the depositor rod in place and insulate its heat.

\* \* \* \* \*